US011234857B2

(12) United States Patent
Miller et al.

(10) Patent No.: US 11,234,857 B2
(45) Date of Patent: Feb. 1, 2022

(54) TUNABLE STIFFNESS MENSTRUAL DEVICE

(71) Applicant: The Flex Company, Venice, CA (US)

(72) Inventors: Andrew Ross Miller, Venice, CA (US); Jane Hartman Adamé, Venice, CA (US); Lauren Schulte Wang, Venice, CA (US); Clementine Dakota Gilbert, New York, NY (US)

(73) Assignee: The Flex Company, Venice, CA (US)

( * ) Notice: Subject to any disclaimer, the term of this patent is extended or adjusted under 35 U.S.C. 154(b) by 0 days.

(21) Appl. No.: 17/222,925

(22) Filed: Apr. 5, 2021

(65) Prior Publication Data

US 2021/0307954 A1     Oct. 7, 2021

Related U.S. Application Data

(60) Provisional application No. 63/004,931, filed on Apr. 3, 2020, provisional application No. 63/035,520, filed on Jun. 5, 2020, provisional application No. 63/136,539, filed on Jan. 12, 2021.

(51) Int. Cl.
*A61F 5/455*     (2006.01)
*A61F 5/44*     (2006.01)

(52) U.S. Cl.
CPC .......... *A61F 5/4553* (2013.01); *A61F 5/4404* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,891,761 A | * | 12/1932 | Goodard | A61F 5/4553 604/330 |
| 1,996,242 A | * | 4/1935 | Hagedorn | A61F 5/4553 604/330 |
| 2,089,113 A | * | 8/1937 | Chalmers | A61F 5/4553 604/330 |
| 2,321,340 A | * | 6/1943 | Waterbury | B29C 70/70 264/250 |
| 2,534,900 A | * | 12/1950 | Chalmers | A61F 5/4553 604/330 |
| 2,616,426 A | * | 11/1952 | Gordon | A61F 5/4553 604/330 |
| 3,128,767 A | * | 4/1964 | Nolan | A61F 6/08 604/330 |
| 3,216,422 A | * | 11/1965 | Steiger | A61F 6/08 604/330 |
| 3,404,682 A | * | 10/1968 | Waldron | A61F 13/266 604/330 |
| 3,626,942 A | * | 12/1971 | Waldron | A61F 5/4553 604/330 |

(Continued)

FOREIGN PATENT DOCUMENTS

WO     2020136380 A2     7/2020

*Primary Examiner* — Guy K Townsend
(74) *Attorney, Agent, or Firm* — Haynes and Boone, LLP

(57) ABSTRACT

A menstrual device with a reservoir portion and a rim portion where the rim element is comprised of stiffer higher durometer resilient material while the reservoir portion is made from a softer lower durometer material. Additionally, other portions of the menstrual device may have differing durometer materials. The menstrual device may be configured with a compression relief element to help improve the overall folding of the device for use.

7 Claims, 15 Drawing Sheets

(56) References Cited

U.S. PATENT DOCUMENTS

| | | | | |
|---|---|---|---|---|
| 3,841,333 | A * | 10/1974 | Zalucki | A61F 5/4553 604/330 |
| 3,845,766 | A * | 11/1974 | Zoller | A61F 5/4553 604/330 |
| 4,198,965 | A * | 4/1980 | Strickman | A61F 6/08 128/832 |
| 4,381,771 | A * | 5/1983 | Gabbay | A61F 6/08 128/836 |
| 4,799,929 | A * | 1/1989 | Knowles | A61F 5/4553 604/331 |
| 4,848,363 | A * | 7/1989 | Cattanach | A61F 5/4553 128/834 |
| 4,961,436 | A * | 10/1990 | Koch | A61F 6/08 128/834 |
| D323,212 | S * | 1/1992 | Crawford | D24/121 |
| 5,295,984 | A * | 3/1994 | Contente | A61K 9/0036 604/317 |
| 5,827,248 | A * | 10/1998 | Crawford | A61F 5/4553 604/328 |
| 5,928,249 | A * | 7/1999 | Saadat | A61B 17/42 606/119 |
| 5,947,992 | A * | 9/1999 | Zadini | A61F 13/2045 606/193 |
| 6,126,616 | A * | 10/2000 | Sanyal | A61B 10/0291 128/834 |
| 6,168,609 | B1 * | 1/2001 | Kamen | A61F 5/4553 600/573 |
| 6,241,846 | B1 * | 6/2001 | Contente | B29C 65/7867 156/378 |
| 6,264,638 | B1 * | 7/2001 | Contente | A61F 5/4553 604/285 |
| 6,332,878 | B1 * | 12/2001 | Wray | A61F 5/4553 604/328 |
| 6,796,973 | B1 * | 9/2004 | Contente | A61F 5/4553 128/832 |
| 7,845,355 | B2 * | 12/2010 | Moench | A61F 6/08 128/833 |
| 8,454,493 | B2 * | 6/2013 | La Vean | A61F 6/08 600/33 |
| 8,690,847 | B2 * | 4/2014 | Norman | A61F 5/4553 604/330 |
| 8,795,248 | B2 * | 8/2014 | Shihata | A61F 5/4553 604/385.17 |
| 9,357,982 | B2 * | 6/2016 | Edmunds | A61B 10/02 |
| D760,897 | S * | 7/2016 | Teo | D24/141 |
| 10,016,308 | B2 * | 7/2018 | Knox | A61F 15/005 604/330 |
| D832,438 | S * | 10/2018 | Brockway | D24/141 |
| D836,196 | S * | 12/2018 | Ahn | D24/141 |
| D841,808 | S * | 2/2019 | Drach | D24/141 |
| D852,361 | S * | 6/2019 | Sedic | D24/141 |
| D852,362 | S * | 6/2019 | Sedic | D24/141 |
| D864,390 | S * | 10/2019 | Sedic | D24/141 |
| D892,324 | S * | 8/2020 | Yi | D24/141 |
| D894,386 | S * | 8/2020 | LeClerc | D24/141 |
| D895,798 | S * | 9/2020 | Newman | D24/141 |
| D895,799 | S * | 9/2020 | Newman | D24/141 |
| D895,800 | S * | 9/2020 | Knox | D24/141 |
| 10,959,873 | B2 * | 3/2021 | Wilson | A61F 5/4553 |
| 2008/0077097 | A1 * | 3/2008 | Chambers | A61F 5/4553 604/330 |
| 2008/0200888 | A1 * | 8/2008 | Gooch | A61F 5/4553 604/330 |
| 2008/0209638 | A1 | 9/2008 | Unger | |
| 2010/0242968 | A1 * | 9/2010 | Vean | A61F 6/08 128/830 |
| 2010/0312204 | A1 * | 12/2010 | Sheu | A61F 6/08 604/330 |
| 2013/0110060 | A1 * | 5/2013 | Shihata | A61F 5/4553 604/330 |
| 2015/0164680 | A1 * | 6/2015 | Chen | A61F 5/4553 604/330 |
| 2016/0278988 | A1 * | 9/2016 | Knox | A61F 15/005 |
| 2017/0189222 | A1 * | 7/2017 | Lin | A61F 5/4553 |
| 2018/0028350 | A1 * | 2/2018 | Wilson | A61F 5/4553 |
| 2018/0199874 | A1 * | 7/2018 | Hwang | A61B 6/847 |
| 2018/0214298 | A1 * | 8/2018 | Medas | A61F 5/4553 |
| 2019/0021898 | A1 * | 1/2019 | Ahn | A61F 5/441 |
| 2019/0083296 | A1 * | 3/2019 | Miller | A61F 5/4553 |
| 2019/0282350 | A1 * | 9/2019 | Conti | A61F 2/0095 |
| 2019/0314191 | A1 * | 10/2019 | Bobarikin | A61F 5/4553 |
| 2019/0336318 | A1 * | 11/2019 | Kubo | A61F 5/4553 |
| 2019/0358077 | A1 * | 11/2019 | Bauer | A61F 5/4553 |
| 2020/0046572 | A1 * | 2/2020 | Hwang | A61F 5/455 |
| 2020/0060864 | A1 * | 2/2020 | Font Caselles | A61F 5/4553 |
| 2020/0078208 | A1 * | 3/2020 | Stoebe-Latham | A61F 5/4553 |
| 2020/0078209 | A1 * | 3/2020 | Stoebe-Latham | A61F 13/55175 |
| 2020/0113500 | A1 * | 4/2020 | Hwang | A61F 5/4553 |
| 2020/0206019 | A1 * | 7/2020 | Brown | A61F 5/4553 |
| 2020/0214876 | A1 * | 7/2020 | Tsai | A61F 5/4553 |

* cited by examiner

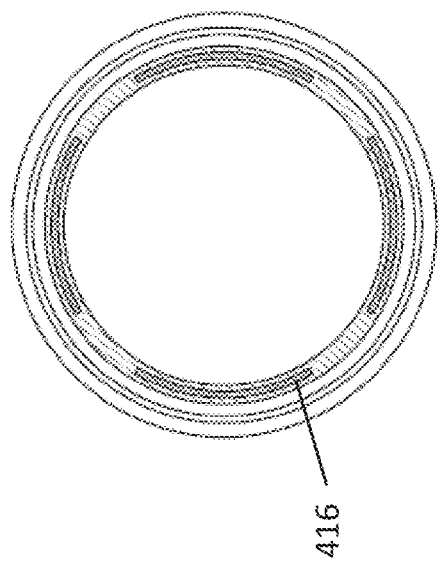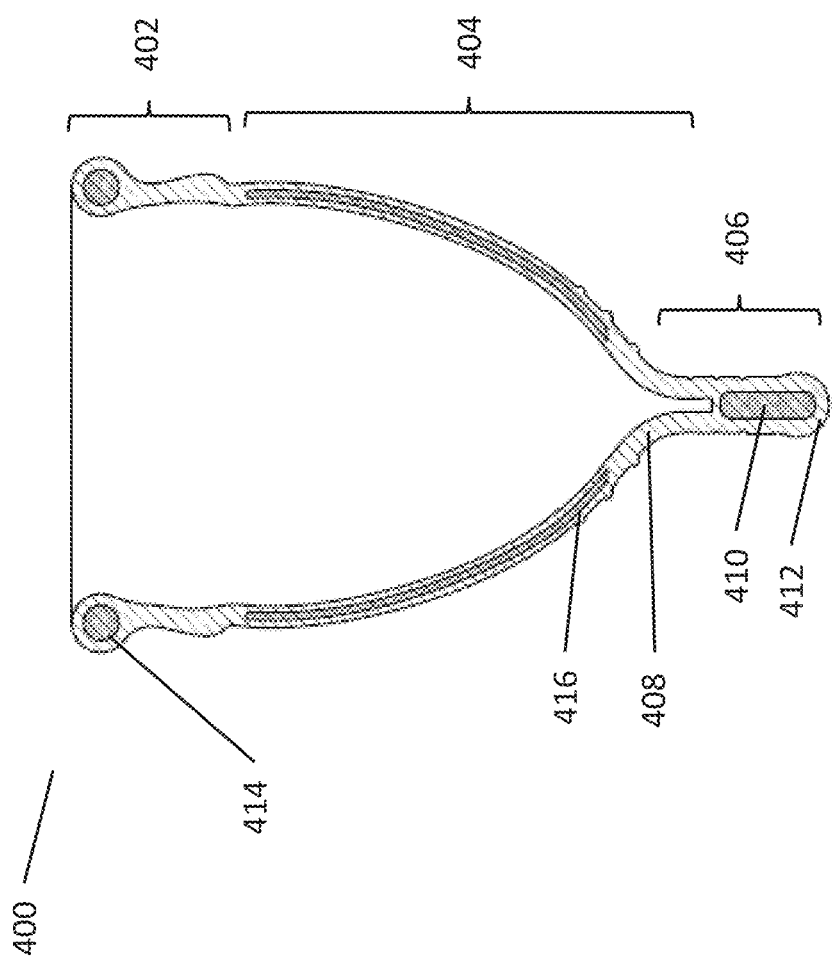
Fig. 4B
Fig. 4A

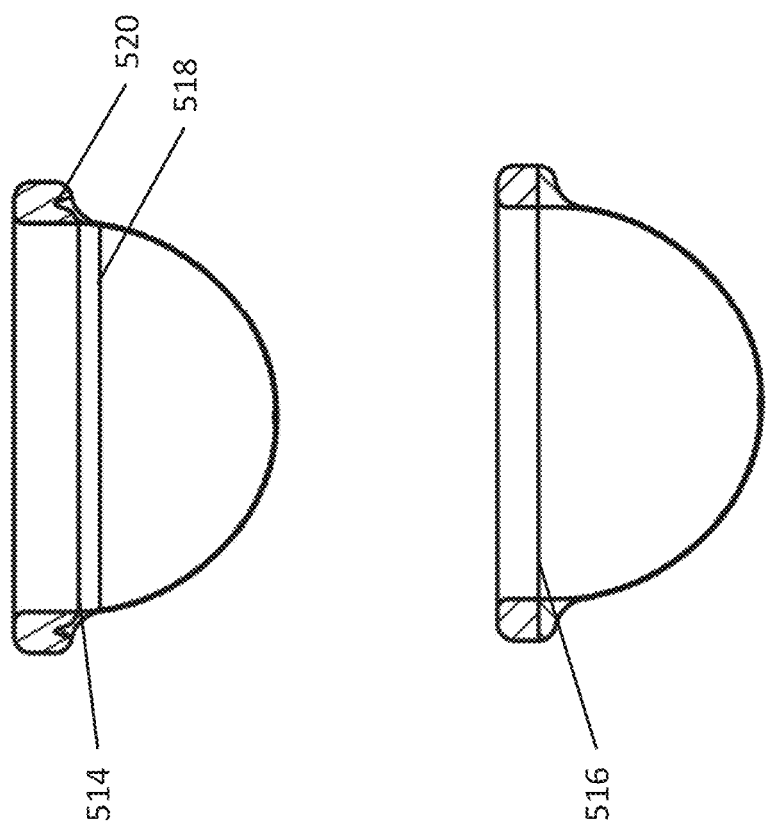
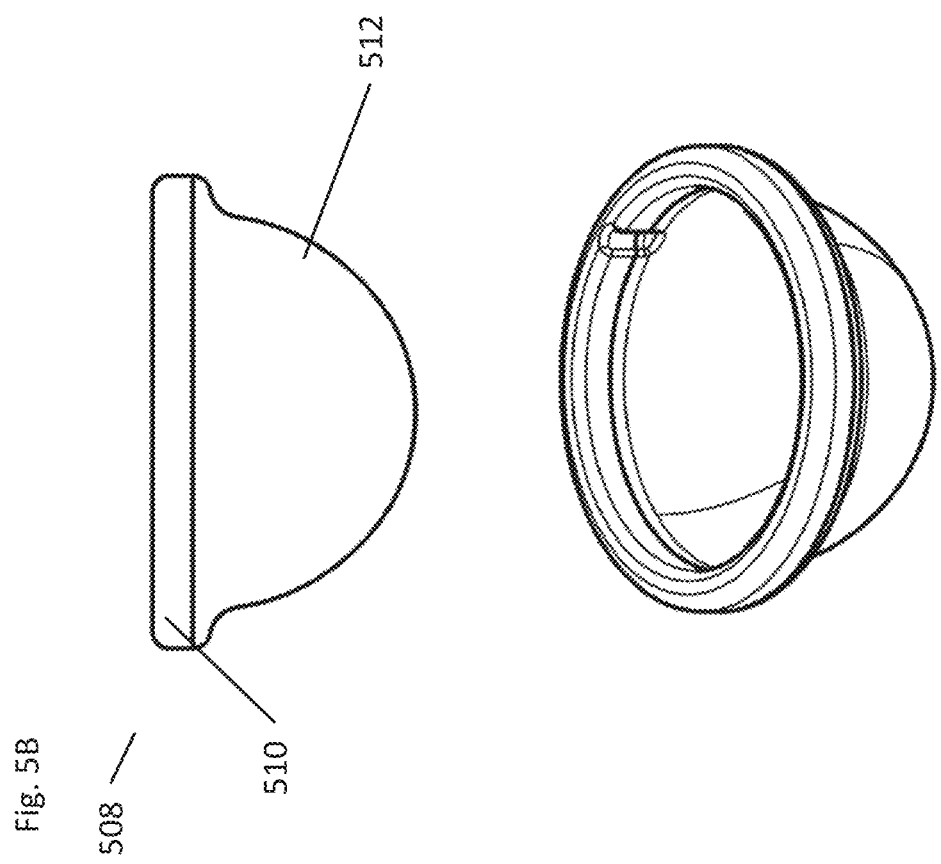
Fig. 5B

| Concept | Image | Description | Volume |
|---|---|---|---|
| Nominal |  | Current design | 0.368 in^3 |
| A |  | Triangular profile | 0.260 in^3 |
| B |  | U shape profile | 0.256 in^3 |
| C |  | Shorter rim height | 0.219 in^3 |
Fig. 6

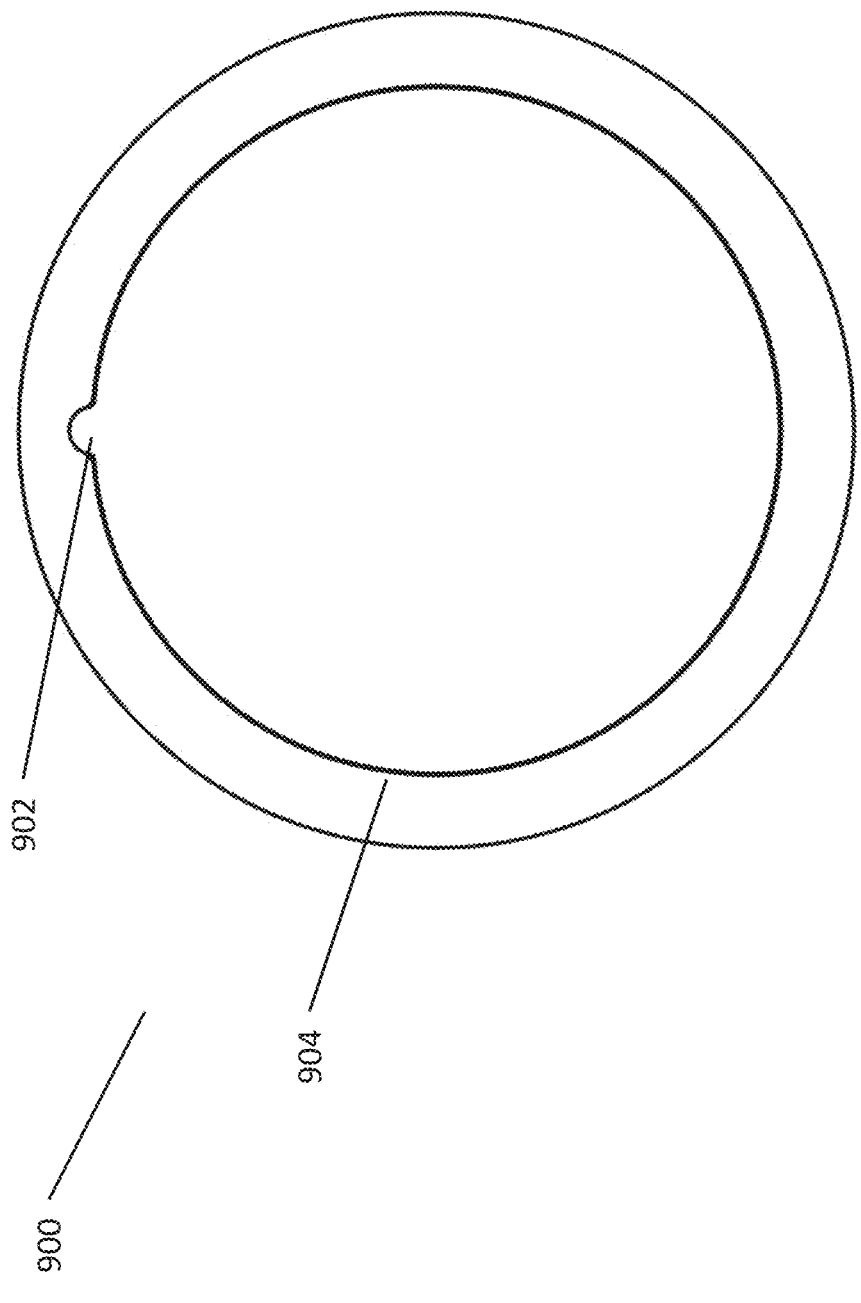

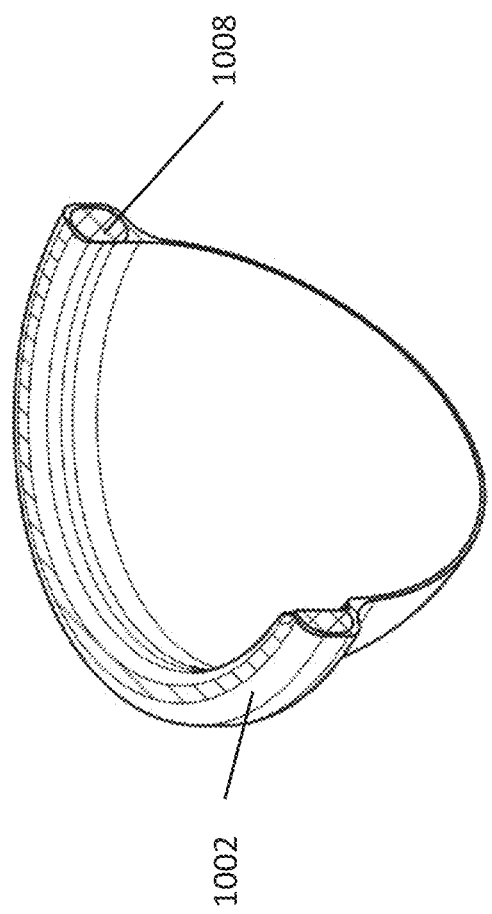
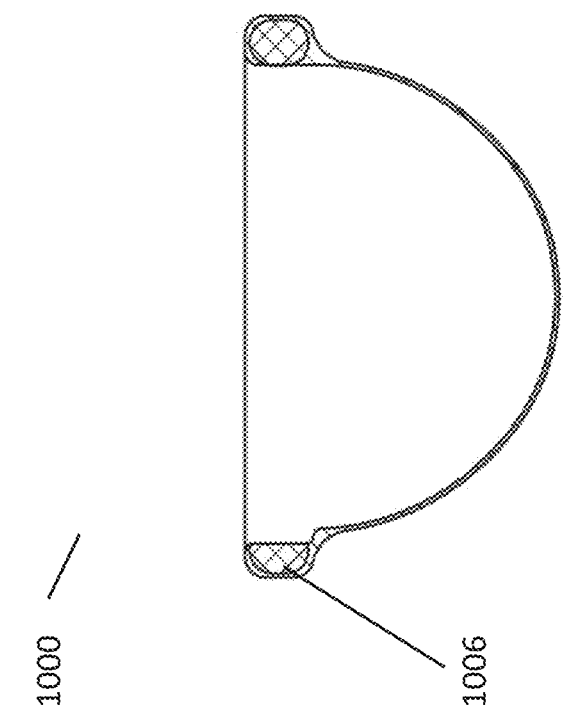

TUNABLE STIFFNESS MENSTRUAL DEVICE

CROSS-REFERENCED APPLICATIONS

This application claims priority to U.S. Provisional Applications 63/004,931 filed on Apr. 3, 2020, and 63/035,520 filed on Jun. 5, 2020, and 63/136,539 filed on Jan. 12, 2021. The disclosures of which are included herein by reference in its entirety

FIELD OF THE INVENTION

The present invention generally relates to menstrual collection devices, specifically menstrual discs and/or menstrual cups.

BACKGROUND OF THE INVENTION

A person who menstruates will typically use a tampon or pad to absorb catamenial fluids. Alternatives to tampons and pads exist to collect catamenial fluids such as menstrual cups and/or menstrual discs. Menstrual cups have been in use and have been known as is described further in U.S. Pat. No. 1,891,761 to Goddard, U.S. Pat. No. 1,996,242 to Hagedorn, U.S. Pat. No. 2,089,113 to Chalmers, U.S. Pat. No. 5,827, 248 to Crawford, and U.S. Design Pat. No. D323,212 to Crawford. Such devices are commonly used as a replacement to other catamenial devices such as tampons and sanitary napkins.

The typical menstrual cup is a cup-like device with a reservoir or catchment area and a rim designed to be inserted into the vagina and catch menses. Goddard, Hagedorn, and Chalmers devices are worn in a lower region of the vaginal canal where there are more nerve endings. These menstrual cups form a vacuum seal with the vaginal wall that must be disrupted before the cup is removed.

Menstrual devices are generally designed to have resilient features such that the device can be compacted for insertion and then return to a deployed or non-compacted state for use. Additionally, the level of resiliency can vary from device to device and manufacturer to manufacturer because every end user has a different level of comfort associated with each device. Many manufacturers tend to produce a variety of different devices with different levels of stiffness and/or resiliency in an attempt to accommodate a wider consumer base. Moreover, manufactures still follow traditional manufacturing methods and materials which tend to limit the ability to capture a larger consumer base.

BRIEF SUMMARY OF THE INVENTION

Many embodiments are directed to menstrual devices, specifically menstrual devices that are manufactured with materials having different durometers placed strategically within the device to improve the level of comfort and device effectiveness. Additionally, many embodiments may incorporate one or more compression relief notch within the rim to help improve foldability of the device for use.

Many embodiments are directed to a menstrual device with a body portion that has an exterior surface and an interior surface and is made of a material that has a first durometer. The body generally forms a circular shape and the interior surface defines a reservoir and the exterior surface defines a first diameter. The device further has a resiliently foldable rim connected to the body portion and is made of a material that has a second durometer that is higher than the first durometer.

In other embodiments, the menstrual device has an internal rim support element disposed within the resiliently foldable rim and wherein the internal support element is made of a material having a third durometer. comprises the full thickness of the rim.

In still other embodiments, the menstrual device has a plurality of ridges disposed along a section of the body portion of the menstrual device, wherein the plurality of ridges are made of material having a durometer that is higher than that of the first durometer.

In yet other embodiments, the body portion comprises an internal stiffener element disposed between the exterior surface and the interior surface and wherein the internal stiffener element is made of a material with a higher durometer than the first durometer.

In still yet other embodiments, the internal stiffener element is made of the different material from that of the body portion.

In other embodiments, the menstrual device has a stem element connected to a bottom portion of the body, wherein the stem element has an elongated body that extends from the body portion downward beneath the body portion.

In still other embodiments, the stem further comprises an internal stem disposed within the elongated body, wherein the internal stem is made of a different material from that of the stem.

In yet other embodiments, the rim has a cross sectional shape selected from a group consisting of triangular, "U" shaped, and curved upper and lower edges.

Other embodiments are directed to a menstrual device with a body portion having an exterior surface and an interior surface defining a generally circular shape, wherein the interior surface defines a reservoir and wherein the exterior surface defines a first diameter. The device also has a resiliently foldable rim connected to the body portion having an outer diameter and an inner diameter wherein the outer diameter is larger than the first diameter, wherein the rim has a predefined height and a thickness. The rim is configured with a compression relief element disposed within the resiliently foldable rim such that it extends from the inner diameter to a distance that is less than the predefined thickness.

In still yet other embodiments, the compression relief element is a notch of removed material.

In other embodiments, the notch has a cross section selected from a group consisting of "V" shaped, semicircle, and quarter circle.

In still other embodiments, the compression relief element is a portion of the rim that is thinner than the remainder of the rim such that the thickness of the rim is less that the predefined thickness.

In yet other embodiments, the portion of the rim that is thinner is between 0.1 and 15 degrees wide.

In still yet other embodiments, the portion of the rim that is thinner is between 15 and 45 degrees wide.

In other embodiments, the portion of the rim that is thinner is thinner than the predefined thickness but more than half the predefined thickness.

In still other embodiments, the portion of the rim that is thinner is thinner than half the predefined thickness.

In yet other embodiments, the predefined height is between 5 and 16 mm high.

In still yet other embodiments, the predefined thickness is between 3 and 10 mm.

In other embodiments, the resiliently foldable rim is generally a hollow tube running circumferentially around a top of the body and wherein the hollow tube has a plurality of lattice support elements disposed within the tube thereby providing a resilient support element within the rim.

In still other embodiments, the compression relief notch has a transition point between the notch and a main body of the rim, and wherein the transition point is a sharp defined edge.

In yet other embodiments, the compression relief notch has a transition point between the notch and a main body of the rim, and wherein the transition point is a smooth edge.

In still yet other embodiments, the body portion and the resiliently foldable rim are made from the same material.

In other embodiments, the menstrual device has a transition location between the materials of different durometers.

In still other embodiments, the transition location is positioned in a location selected from a group consisting of within the rim, within the catchment portion, and at a secondary transition between the rim and the catchment portion.

In yet other embodiments, at least two compression relief elements disposed within the resiliently foldable rim such that it extends from the inner diameter to a distance that is less than the predefined thickness.

In still yet other embodiments, the body portion and the resiliently foldable rim are made from different materials.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

The description will be more fully understood with reference to the following figures, which are presented as exemplary embodiments of the invention and should not be construed as a complete recitation of the scope of the invention, wherein:

FIG. 4A illustrates a cross sectional view of a menstrual device with a resilient rim with multiple durometer materials in accordance with embodiments of the invention.

FIG. 4B illustrates a top cross-sectional view of a menstrual device with resilient ridges in accordance with embodiments of the invention.

FIG. 5B illustrates various views of a menstrual device with varying durometer materials in accordance with embodiments of the invention.

FIG. 6 is a tabular illustration of various rim cross sections in accordance with several embodiments of the invention.

FIGS. 9A and 9B illustrate a menstrual device with a compression relief notch in the rim in accordance with embodiments of the invention.

FIGS. 10A and 10B illustrate a menstrual device with compression relief designs in the rim in accordance with embodiments of the invention.

DETAILED DESCRIPTION OF THE INVENTION

Figure 1:
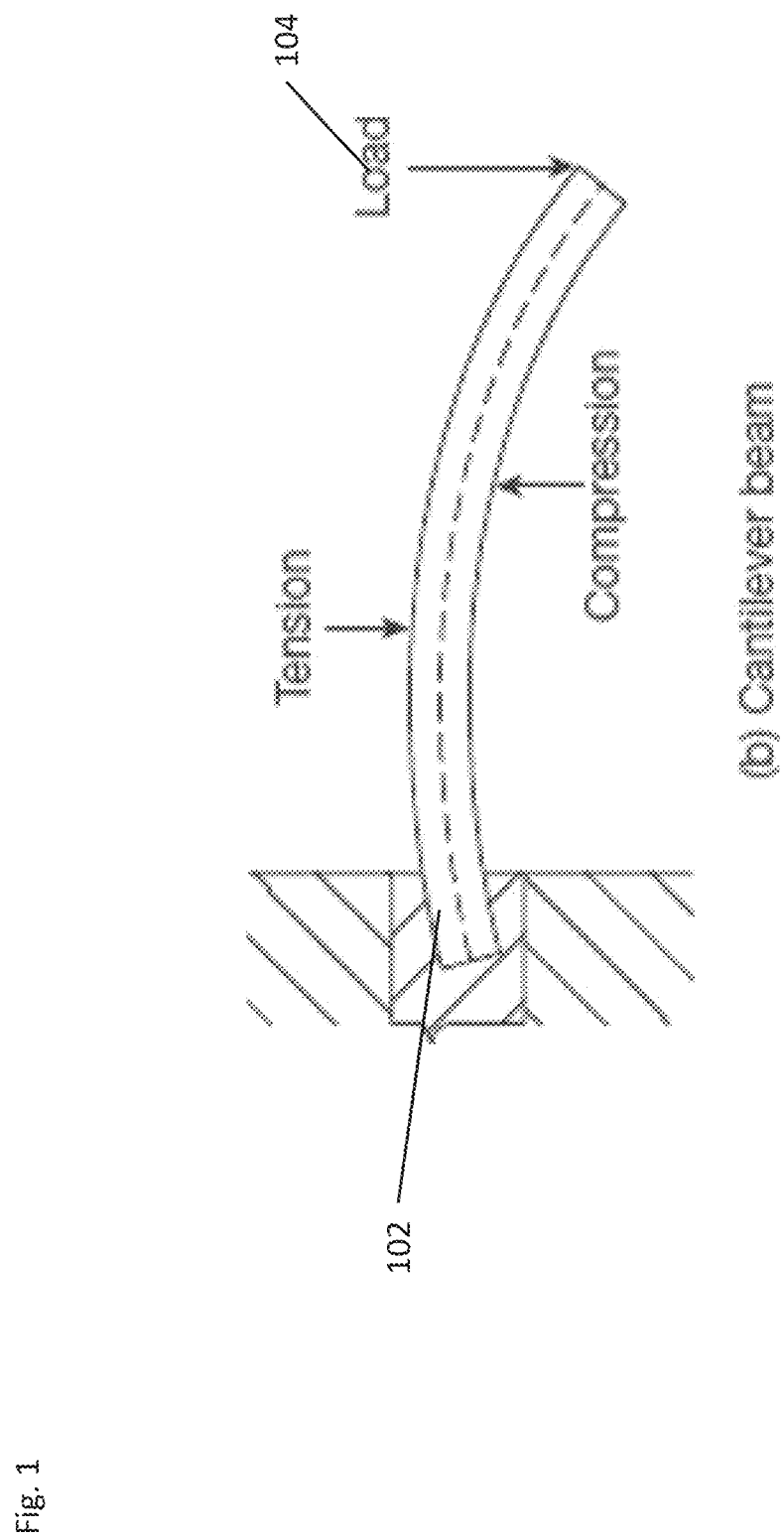
FIG. 1 illustrates a bending moment of a cantilever beam

Turning now to the drawings, systems and methods of a menstrual device with a number of alternative features that can allow for improved use such as multiple durometer materials as well as embedded geometric features are described. In many embodiments of the invention, the menstrual device contains a resilient rim connected to a reservoir portion where the rim and reservoir are foldable such that it can be folded and inserted into a vaginal canal. In accordance with various embodiments, the rim of the device may contain multiple durometer materials. For example, an internal portion of the rim may have a higher durometer material that is stiffer and subsequently the external portion or a portion of the rim surrounding the internal portion may have a softer or lower durometer material. Additionally, many embodiments may have multiple durometers in various other portions of the menstrual device, such as the catchment area or the removal aid portion. In a number of various embodiments, the rim may be configured with one or more notches or geometric spaces that can allow for improved bending capabilities of the rim to help improve the insertion of the device.

The term "durometer" is known within the art as a measure of hardness of material such as plastic, rubber, silicone, or any other non-metallic material. In addition to the general definition known in the art, "durometer" within the context of the application can refer to the relative stiffness of the material. Therefore, when one material has a durometer that is greater than another material it may be considered to be stiffer than the other material. The opposite is also true.

The stiffness or level of resiliency of a menstrual device can affect the insertion, comfort, fit, leak protection and removal of the menstrual devices specifically, menstrual cups and discs must deform to a collapsed shape for insertion and have enough resilience to hold shape when inserted and to spring open once inserted. Once inserted, the product must hold its shape while conforming to the anatomy to provide a leak resistant fit and seal. Such resilient features tend to require a stiffer material in order to perform accordingly. Meanwhile, the device must be compliant enough to adapt to the body in different activities and body positions while being comfortable. Ideally, a product is imperceptible when worn. These various ideal properties of cups and discs have competing engineering considerations. A stiffer cup is easier to open once inserted but harder to collapse into shape for insertion. Moreover, a stiffer cup maintains a position better within the user in a variety of activities. However, stiffer materials tend to be more perceptible to the user. As a result, various devices on the market are sold to be stiffer or less stiff to accommodate different customer preferences. Existing products also try to modulate stiffness in different regions by changing thickness, inserting localized areas of thickness like ridges. The clearest example are devices which provide ridging to help translate compressive forces at the base of the cup to aid in the deformation required to break the seal for most traditional cups before removal. However, such devices tend to lead to a large number of different devices that can saturate the market and may not be comfortable to the end user. Furthermore, existing menstrual discs and cups often do not maintain a compressed shape on insertion through the vaginal canal and instead tend to flare open during insertion leading to difficulty and discomfort for the user.

Increasing the stiffness of the rim region of the device increases the device's ability to maintain a compressed shape under loading conditions of insertion. However, the geometric designs of existing menstrual discs and cups limit the usefulness of many higher stiffness materials such as a high durometer silicone. The net effect of these competing engineering constraints is that traditional geometric designs limit the size and shape of the device that will naturally require a compressed or folded configuration while maintaining rigidity in that compressed shape.

Figure 2:
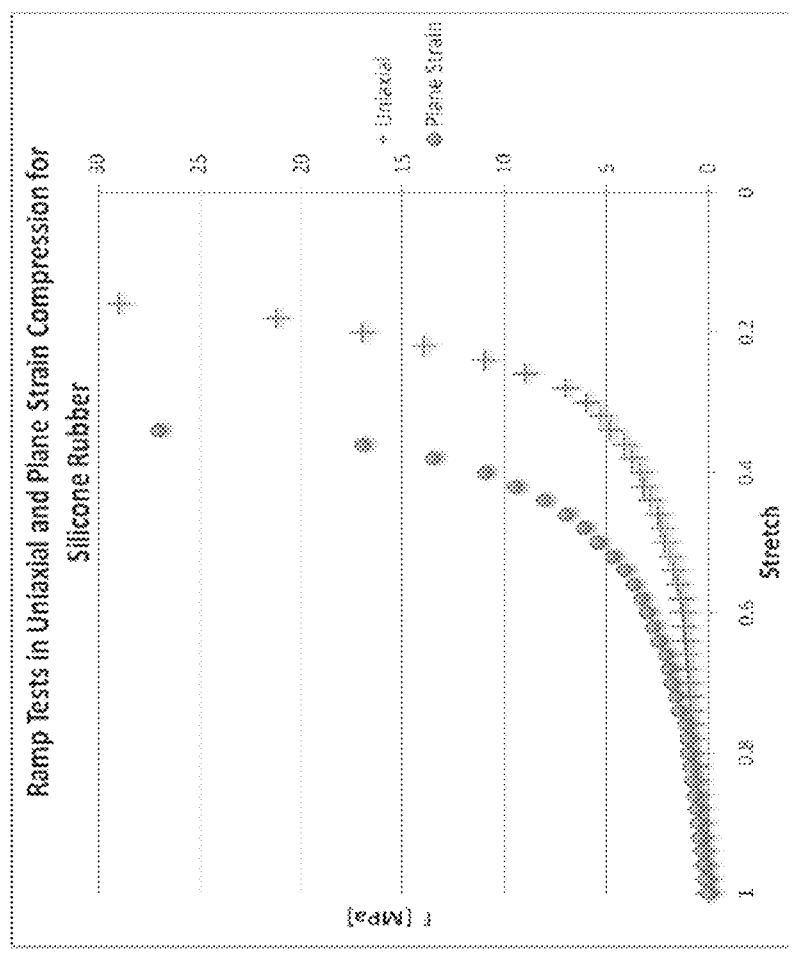
FIG. 2 is a graphical illustration of a stress strain relationship for silicone rubber.

For example, the bending of a beam fundamentally illustrates the same mechanics as the bending of the rim of menstrual cup devices. As illustrated in FIG. 1 a beam 102 under a load 104 will undergo both tension and compression. Given the description of the bent beam, it can be understood that the rim of a menstrual device will undergo similar forces when being folded for insertion. For example, half of the rim material will be in tension while the other half will be in compression. The portion in compression will be limited by the inherent compressibility of the material. Many materials including silicone have a non-linear response to compression at certain loading conditions. In other words, beyond a linear region of strain to stress relationship, these materials will have required non-linearly increasing or exponential strain to accomplish an equivalent increment in strain. Such stress and strain relationships can be illustrated in the graph shown in FIG. 2.

This stress/strain relationship can be especially important in the use of menstrual disc and/or cups as they are requiring to be folded for insertion. Menstrual discs, for example, are typically pinched at the center by a user, forming two lobes, one on the leading end of the device and one on the non-leading end. Each of the lobes undergo both tension and compression and is ultimately designed to expand and widen on insertion. More rigid material tends to produce wider lobes due to the material properties. Accordingly, leading lobes under traditional configurations will be wide and stiff which can present difficulties with insertion. Many embodiments described herein are directed to improvements to the geometry and material properties of the rim that allow for reduced width and improved flexibility of the leading lobe while maintaining or improving the material stiffness that maintains or increases the transfer of force along the device during insertion before buckling.

Embodiments of a Menstrual Device with Multiple Durometer Material

Figure 3A:
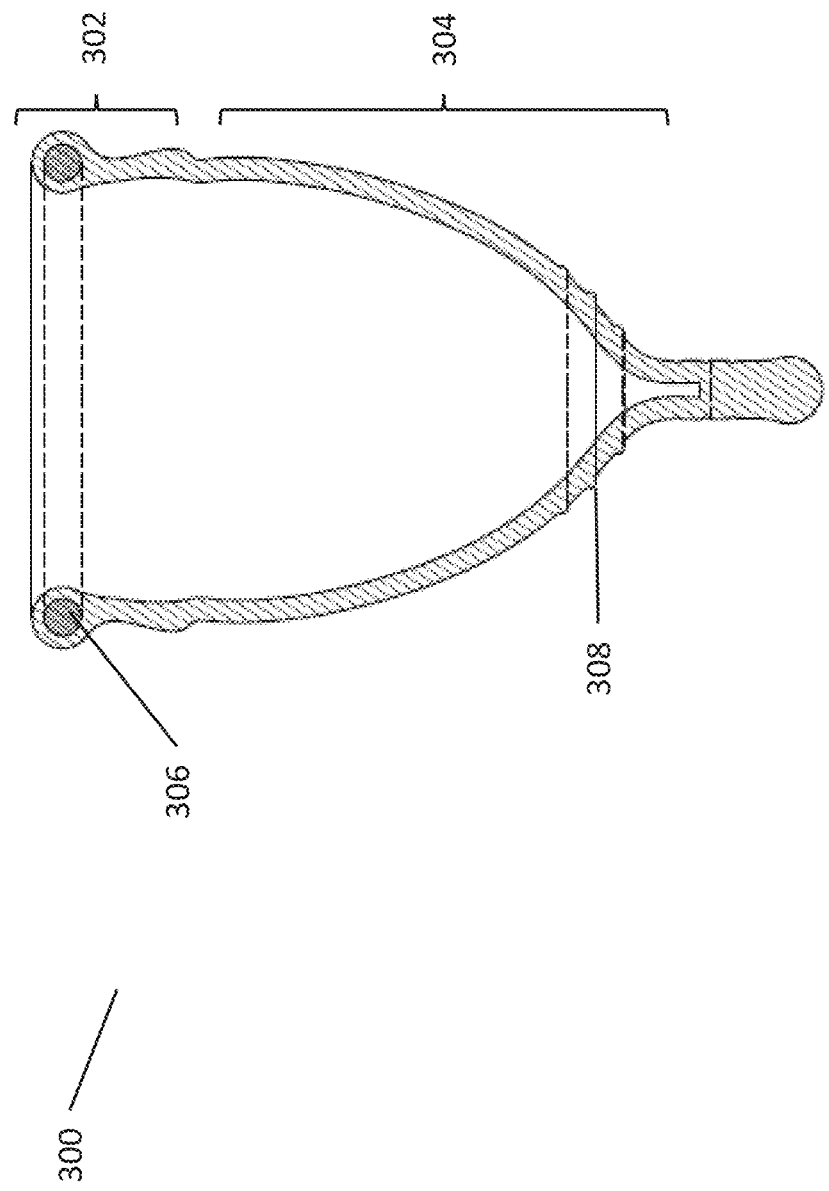
FIG. 3A illustrates a cross sectional view of a menstrual device with multiple durometer materials in different locations in accordance with several embodiments of the invention.

Turning now to the figures, many embodiments of a menstrual device that is manufactured of multiple durometer materials can be seen. FIG. 3 illustrates a menstrual device 300 with a rim 302 and a catchment area 304, similar to most menstrual devices. However, unlike many traditional menstrual devices, many embodiments incorporate an internal rim portion 306 that is made from a higher durometer material. The internal rim portion 306 may be surrounded by a softer and less stiff material that is pliable and capable of bending and forming to the desired shape. The stiffer internal portion 306 may be capable of providing the resilient spring-like functions that are necessary for the device to deploy or be used. However, in accordance with various embodiments, the internal portion 306 is also pliable to a point such that it can be deformed in order to allow for proper insertion of the device into a vaginal canal. In accordance with some embodiments, the catchment portion 304 may be configured with one durometer type material or may be configured with more than one type durometer material. Additionally, many embodiments may add in one or more additional features that can be made of any durometer of material that is suitable for the intended purpose. For example, some embodiments may incorporate ridges 308 along the external portion of the device. The ridges, in many embodiments, can provide a texturing to aid in the removal of the device. In addition, some embodiments may have ridges 308 that are of the same durometer of the catchment portion or may be of a stiffer or higher durometer material similar to that of the internal portion 306. The stiffer ridges 308 may aid in the deployment of the device as well as the removal. Embodiments with multiple durometer materials integrated throughout the device 300 can effectively provide a menstrual device with a tunable stiffness that is fit for a larger number of users.

Accordingly, numerous embodiments may be manufactured in such a way that the rim portion 302 is made of a single durometer material. Additionally, the catchment portion 304 may be made of a second material that is entirely a separate durometer from that of the rim portion 302. Many such embodiments may be manufactured in any number of ways. However, various embodiments may be molded in the same molding process. For example, a first step may mold one portion, either catchment or rim of the specified durometer material. The second step may include the molding of the remaining portion of the device 300. Additionally, some embodiments many utilize a stitching or bonding of the two durometer materials at a given transition point. In some embodiments, silicone may be used in which silicone of different durometers will bond at the stitch point during the molding process.

Figure 3B:
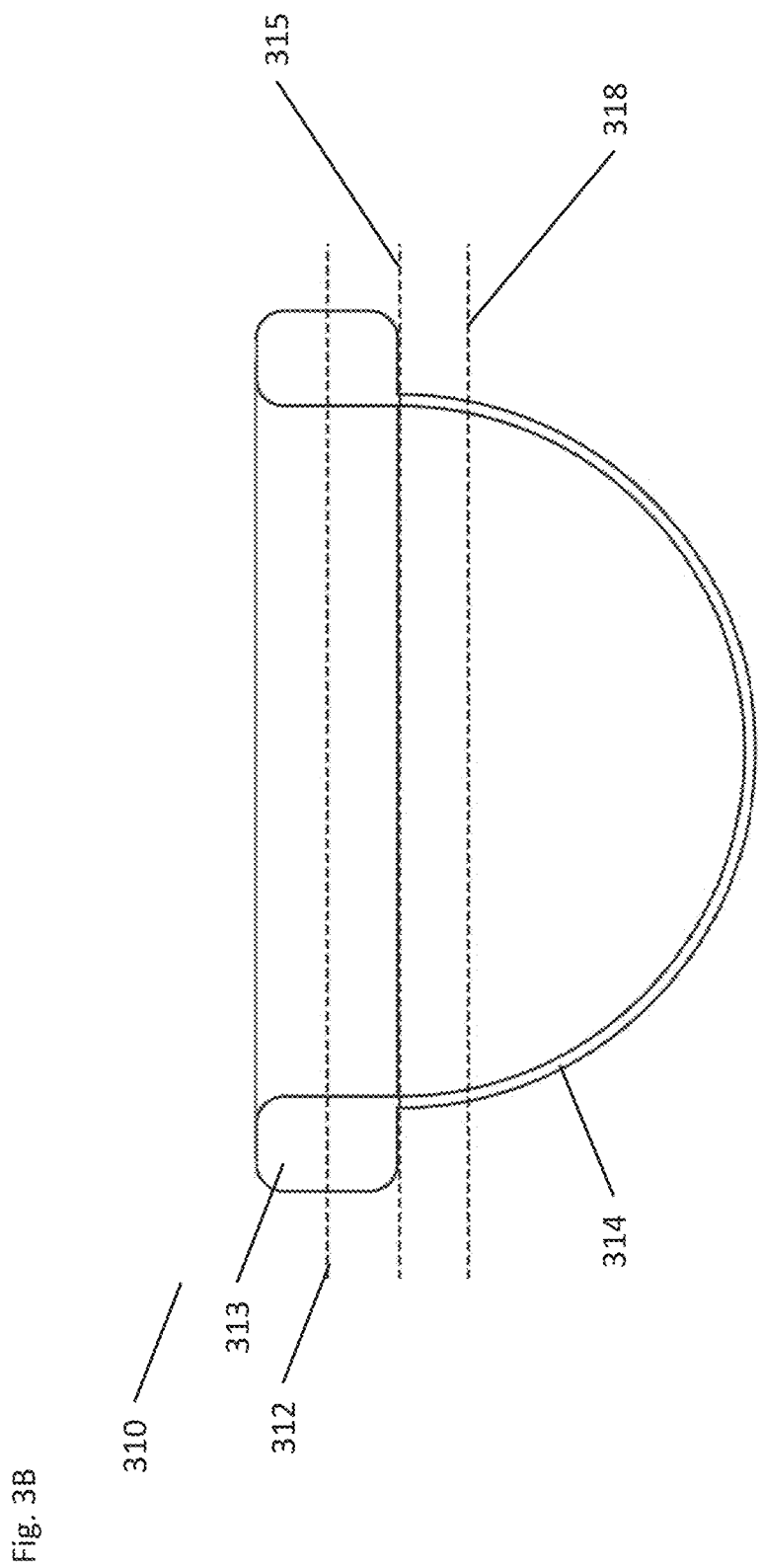
FIG. 3B illustrates a cross sectional view of a menstrual device with varying transition lines in accordance with embodiments of the invention.

As can be appreciated the stitch line or transition between the different materials can be located in a number of different locations. For example, FIG. 3B illustrates a profile of a menstrual device 310 with a span of various stitch line locations. In some embodiments, the stitch line between different materials can be located in an upper portion of the rim, indicated by 312. This can be the point at which the differing durometer materials are molded together during the manufacturing process. It should be understood that the stitch line does not necessarily represent a transition between the rim 313 and a catchment 314, but rather a point where materials of different durometer or different materials transition. Other embodiments many place the stitch line or location at a transition point 315 between the rim 313 and the catchment 314. Still other embodiments may place the stitch line lower within the catchment portion of the cup 318. As can be fully appreciated the transition between the rim 313 and the catchment 314 can vary in accordance with a number of design and/or manufacturing techniques used.

Accordingly, many embodiments can have a number of different transition or stitch lines between different durometer materials. Although specific locations of stitch lines are illustrated, it should be understood that many embodiments can place the stitch line at any desirable location within the device 310.

FIG. 4 illustrates a menstrual device 400 in which some embodiments may be made with multiple durometer materials. Similar to other embodiments, the device 400 may have a rim portion 402 and a catchment portion 404. Additionally, various embodiments may have a stem portion 406 that is connected to the base 408 of the catchment portion 404. In accordance with many embodiments, the stem portion 406 may be configured with more than one durometer material. For example, some embodiments may have an internal stem 410 that is surrounded by an external stem 412. The internal stem 410, according to some embodiments, may have a higher durometer material similar to an internal rim portion 414 within rim 402. In different embodiments, the internal rim portion 414 and the internal stem 410 may have the same or different durometer materials. Additionally, the external stem 412 may be configured with a softer lesser durometer material similar to that of the catchment portion 404 of the device 400. In accordance with various embodiments, the catchment portion 404 as well as the stem portion 406 may have internal stiffener elements 416. Similar to other embodiments, the internal stiffener elements 416 may be of the same or different durometer material as the catchment and/or internal stem 410 and internal rim 414 portions. In accordance with many embodiments, the internal stiffener elements 416 may run vertically up the length of the catchment portion of the device. Additionally, in some embodiments, the internal stiffener elements 416 may be positioned in different locations circumferentially around the catchment portion as illustrated in FIG. 2B. In various embodiments, the internal stiffener elements 416 may be placed within the catchment area 404. In accordance with many embodiments, the internal stiffener elements 416 may be encased within the material that makes up the outer portion of the catchment area. In some embodiments, the internal stiffener elements span the entire thickness of the part such that unique material are dispositioned radially. Additionally, many embodiments may utilize a different durometer material for the internal stiffener elements as is used for the outer material of the catchment area.

Turning now to FIG. 5, other embodiments may be a device 500 in the form of a menstrual disc. Similar to other embodiments, a menstrual disc may have a rim portion 502 and a catchment portion 504. In contrast to other embodiments, a menstrual disc may have a much thinner cross-sectional catchment section as it is designed to be positioned differently within the vaginal canal than that of a menstrual cup seen in FIGS. 3 and 4. Similar to other embodiments, the menstrual disc 500 may be configured with an internal rim portion 506 within rim 502 that has a material of a higher durometer from that of the rest of the device. The internal rim portion 506 may be surrounded by another material with a lower durometer to provide a greater level of comfort for the end user as it would be more compliant to the internal features of the vaginal canal. Additionally, the increased compliance of a softer, lower durometer material can provide better seals and better performance of the device which will ultimately lead to increased user satisfaction.

In accordance with some embodiments, the catchment portion 504 may also be made of one or more durometer materials. For example, a portion of the catchment area 504, such as one half, may have a higher durometer than the remaining portion of the catchment area 504. The higher durometer portion can aid in the interaction of the device 500 with the pubic bone (not shown) when inserted. Accordingly, many embodiments may have an asymmetrical design with respect to the durometer of the materials.

Figure 5A:
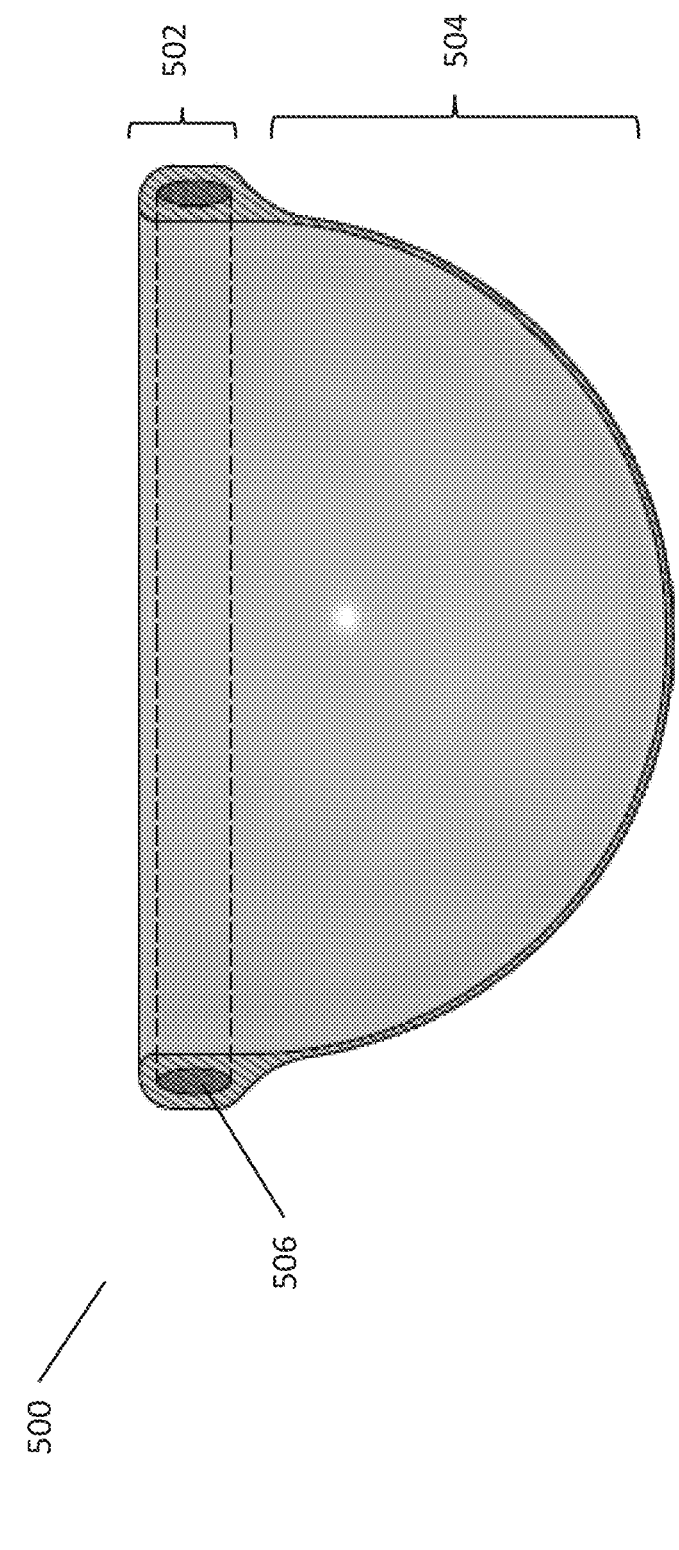
FIG. 5A illustrates a cross sectional view of a menstrual device in accordance with embodiments of the invention.

Although FIG. 5A illustrates embodiments of a menstrual device with an internal element or internal rim that is made of a different durometer material from that of the device, some embodiments may incorporate the different durometer material throughout the rim itself. For example, FIG. 5B illustrates various views of a menstrual device 508 with a rim 510 that is made of a single material. In such embodiments, the rim 510 may be made of a material with a durometer that varies from that of the catchment 512. Accordingly, the manufacturing process of the device 508 may incorporate one or more transition locations 514, 516, 518 that indicate a transition between materials of different durometer. In some embodiments, the rim 510 and the catchment 512 may be made of the same material, but may simply have different durometers. Other embodiments may incorporate different materials for both the rim and the catchment. Accordingly, it should be reasonably understood that any number of different materials can be used in the device and in any combination that is suitable for manufacturing the device. Although, various material transition locations are shown, it should be understood that the transition between materials can be at any location based on the applicable manufacturing process. Additionally, some embodiments may incorporate more than one transition location. Additionally, in some embodiments the transition location may not be a straight line, but rather a contoured or curved transition 520 that changes position depending on the overall design and/or manufacturing method.

As can be appreciated, many embodiments may use one or more durometer materials in the manufacturing of the menstrual device. As illustrated above, numerous embodiments may have a portion or multiple portions of the device made from one durometer type material while the remaining portion(s) are made from a second durometer type material. It can be appreciated that any combination of durometers may be used so as to meet the desired specifications of form, fit, and function of the device. In a number of embodiments, the materials can be the same or may be different materials that correspondingly work with the same and/or different durometers. Additionally, although various embodiments are illustrated, it should be understood that embodiments may be presented individually or in combination with any other embodiments illustrated herein.

Embodiments of the Materials

As described earlier, the durometer or stiffness of the material can be important to the level of comfort for the end user. Accordingly, various embodiments may incorporate a number of different materials that are safe for use as well as have a variety of durometers that can be used throughout embodiments of the device. For example, as shown above with respect to FIGS. 3-5, many embodiments may be configured to use different durometer materials at different locations throughout the device. Therefore, the choice of material can be important such that it would allow for a regular change in durometer at different locations. In many embodiments, silicone may be used as a material of choice. Silicone can be produced in a variety of different durometers. For example, some embodiments may use a 60A durometer on the Shore "A" scale. Other embodiments may have a 50A or 30A or smaller. The larger the value on the A scale the stiffer the material. Accordingly, many embodiments may use a material, such as silicone, with a 60A durometer for the internal rims and/or stem while using a 30A durometer material on the surrounding portions and catchment portion. Some embodiments may use a variety of durometers throughout the entire device. In addition to the large variations in durometers, silicone also has excellent self-adherence properties that would allow for a lower durometer material to be placed adjacent to, on top of or over the higher durometer material while maintaining the structural integrity of the device. For example, the inner rim would not slip or move within a surrounding outer rim while the device is in use or being inserted. Such movement would likely cause failures in the device itself and/or discomfort for the user. Although, silicone is readily discussed, it should be understood that any number of materials can be used so long as the durometer can vary.

Embodiments of the Rim Design

In accordance with many embodiments, the internal potion of the rim can vary in shape and cross section. This may help to accommodate the various types of materials that can be used to produce the many different embodiments of a menstrual device. As illustrated in FIG. 6, the internal rim may have a number of different cross sections. The rim may include "U" shaped rims. The "U" shaped rim may allow for improve surface tension between the higher and lower durometer materials to help prevent movement. Additionally, such shapes may help with the overall fit and function of the device when inserted. For example, a "U" shaped cross-sectional rim may allow for a desirable level of resiliency in the rim while still providing some compliance to conform to the surrounding environment. Accordingly, many embodiments may incorporate different cross-sectional designs such as a gear or a triangle. In some embodiments the internal rim may have a "D" shape or any other desired shape. It can be appreciated that any number of cross sections can be used in any number of embodiments. The rim may have a contoured cross section. Contoured refers generally to a top edge or leading edge of the rim being rounded or angled as illustrated in the table in FIG. 6. Additionally, contoured can refer to a bottom edge of the rim as well. In general, it should be understood that the contoured surface can take on any number of configurations that allow for improved use of the menstrual device.

In accordance with many embodiments, the form, fit, and function of the final product or device can be important. Accordingly, it can be appreciated that the method of manufacture of such devices can play an important role in the production of a quality product that is adaptable to many users. In accordance with many embodiments, menstrual devices described herein, with multiple durometer materials, can be produces using an overmolding process. The overmolding is when a first material is formed and then a second material is molded over the first. The overmolding process allows for a wider range of material combinations and durometers to be used. For example, some embodiments may use a plastic or metallic inner rim portion that is over molded with a softer low durometer silicone type material.

Figure 7B:
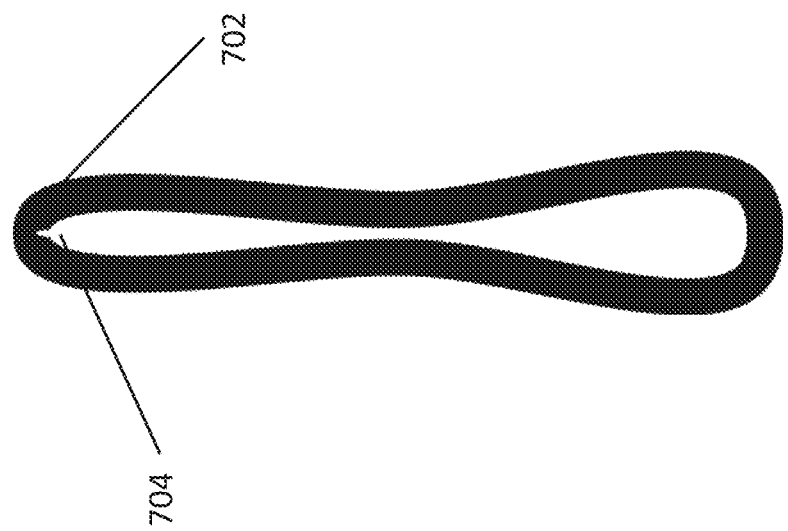
FIG. 7B illustrates a folded rim of a menstrual device with a compression relief in accordance with embodiments of the invention.
Figure 7A:
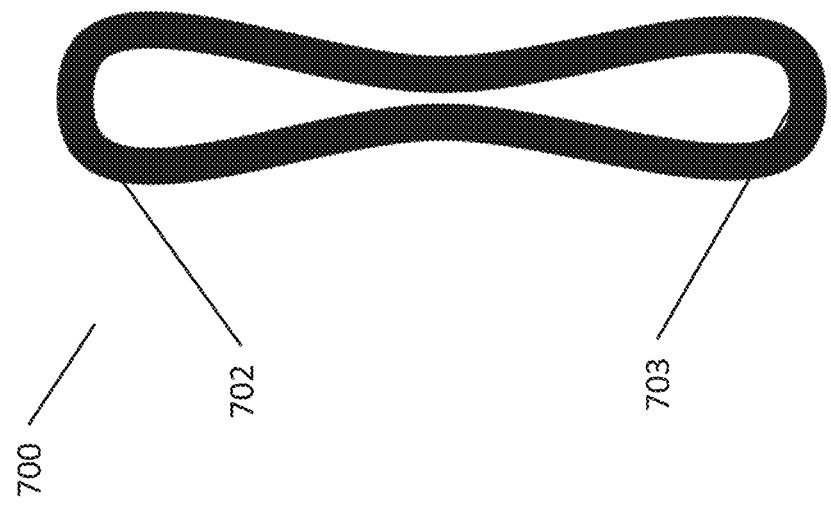
FIG. 7A illustrates a rim of a menstrual device in a folded configuration.

As can be readily appreciated, the rim design of a menstrual device can take on any number of different configurations that can help improved the insertion capabilities of the device. For example, as described above, FIG. 7A illustrates a rim of a menstrual device 700 in a folded state. It can be seen that the folded rim 700 has two lobes (702 & 703) of equal or similar size and shape. This can be based on the material configuration of the rim. Many embodiments may incorporate a relief mechanism as illustrated in FIG. 7B. For example, some embodiments may have a notch 704 that is placed within the rim 700 that allows for a leading lobe 702 to be folded in a tighter or smaller configuration by relieving the compression from folding. While the notch 704 naturally removes material, various embodiments can still allow for the rim 700 to expand once inserted. This can be achieved with the use of multiple durometer materials within the rim specifically designed to allow for improved flexibility as well as strength and resilient response once the pressure from folding is released. As can be further appreciated, the notch itself can serve as an indexing feature on the menstrual device during an overmolding process. This can help to orient the device in the overmold correctly.

Figure 8:
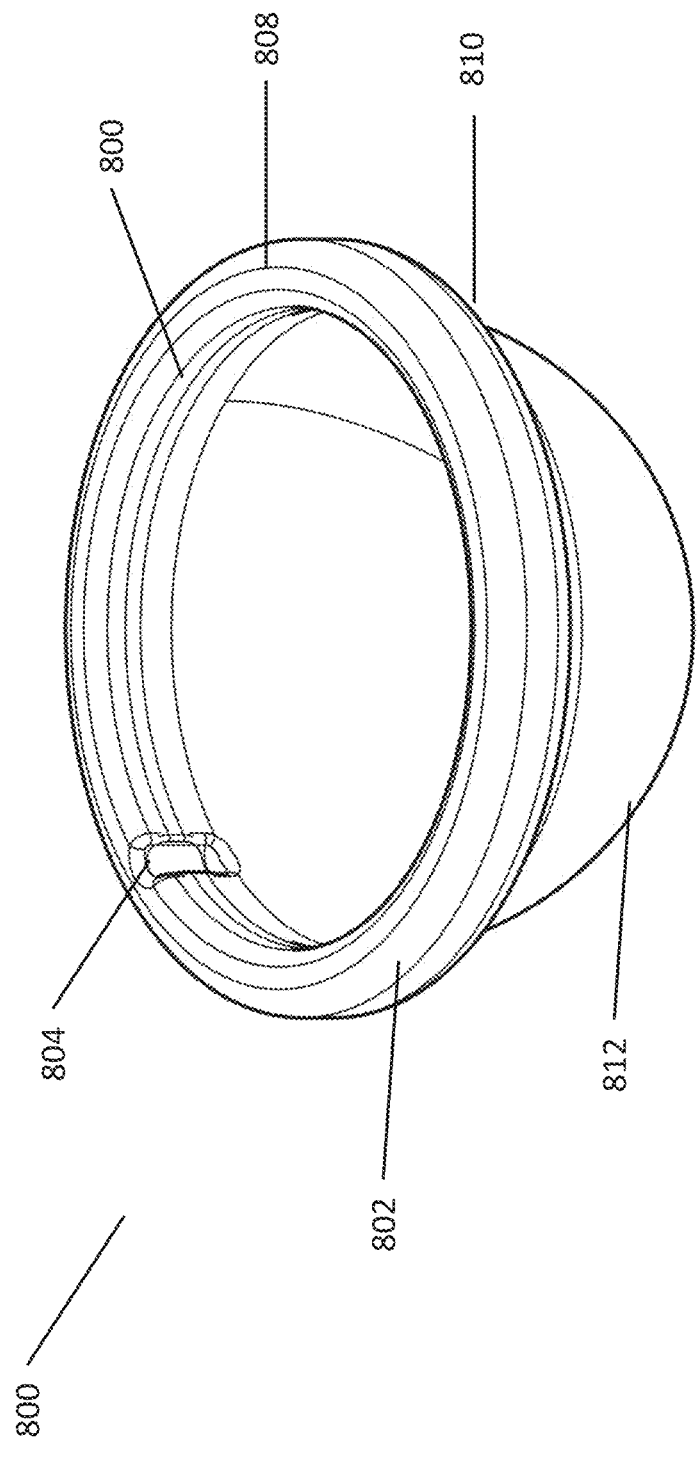
FIG. 8 illustrates a menstrual device with a compression relief element in accordance with embodiments of the invention.
Figure 9B:
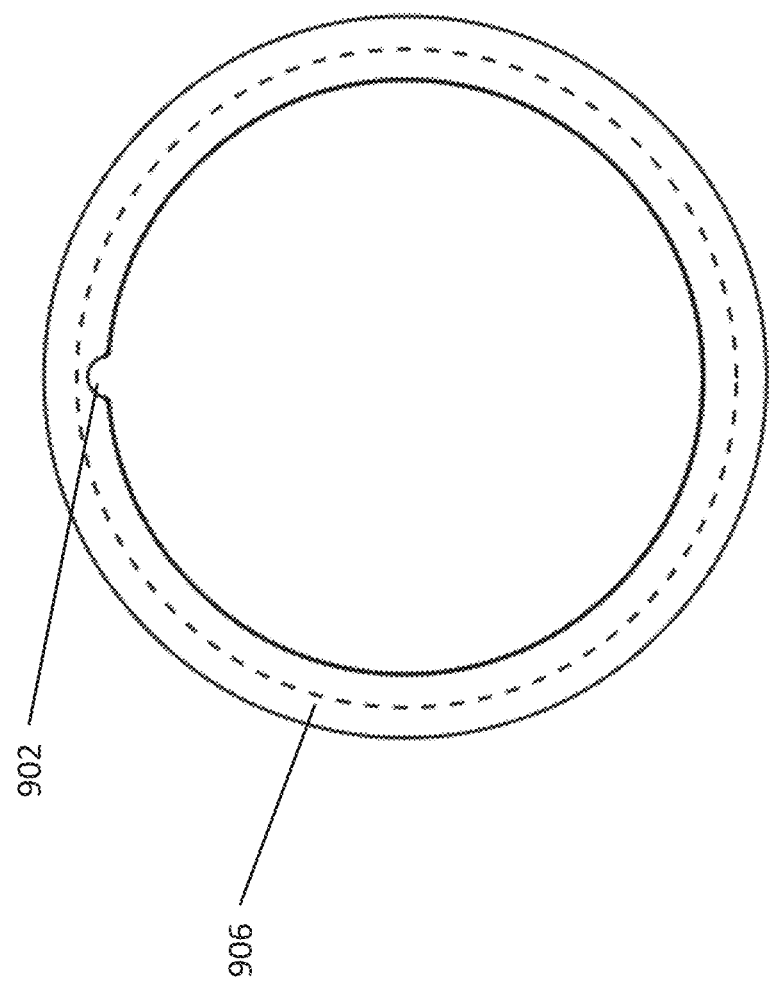

Turning now to FIGS. 8 through 9B various embodiments of relieve mechanisms within a notch can be illustrated. FIG. 8, for example, illustrates a menstrual device 800 with a rim element 802 that has a notch 804 located on the inner portion 806 of the rim 802. The notch 804 can extend through the entire height of the rim, where the height of the rim 802 is defined by the distance between the top 808 and the bottom 810 where the rim connects to a catchment portion 812. The height of the rim, can vary between 5 and 16 mm in accordance with numerous embodiments. Likewise, the thickness of the rim 802 can vary between 3 and 10 mm. The notch 804 can have a number of different shapes and can be contoured in a number of different ways such that it does not extend through the entire thickness of the rim 802, but rather maintains the structural integrity of the rim 802 while providing a compression relief notch 804 to allow for improved folding capabilities. For example, some embodiments of the relief notch 804 may be between 1.5 and 5 mm in depth and may be between 5 and 45 radial degrees wide.

Similarly, FIGS. 9A and 9B illustrate a rim 900 with a notch 902 cut out of an inner portion 904 of the rim 900 of a menstrual device. As seen in FIG. 9B, the notch 902 does not extend past the midline 906 of the rim 902. This can be representative of one particular embodiment to allow for improved folding capabilities as well as help to maintain the structural integrity of the rim 900.

As can be appreciated, improving the flexibility or foldability of the rim of a menstrual device while maintaining the resiliency necessary to expand the rim into place can be done in a number of different ways. In other words, the relief mechanism of the rim can be embodied with a number of alternative features and/or material characteristics that allow for such folding to take place. For example, FIGS. 10A and 10B illustrate cross sectional views of a menstrual device 1000 with a rim 1002 that has one or more decompression features. Additionally, some embodiments may utilize a thinning of the rim in a section. This can be illustrated in FIG. 10A where the leading lobe 1006 is thinner than the trailing lobe 1008. Accordingly, the leading lobe 1006 will fold easier or have a smaller radius than the trailing lobe which is thicker allowing for improved insertion for the menstrual device.

Figure 11:
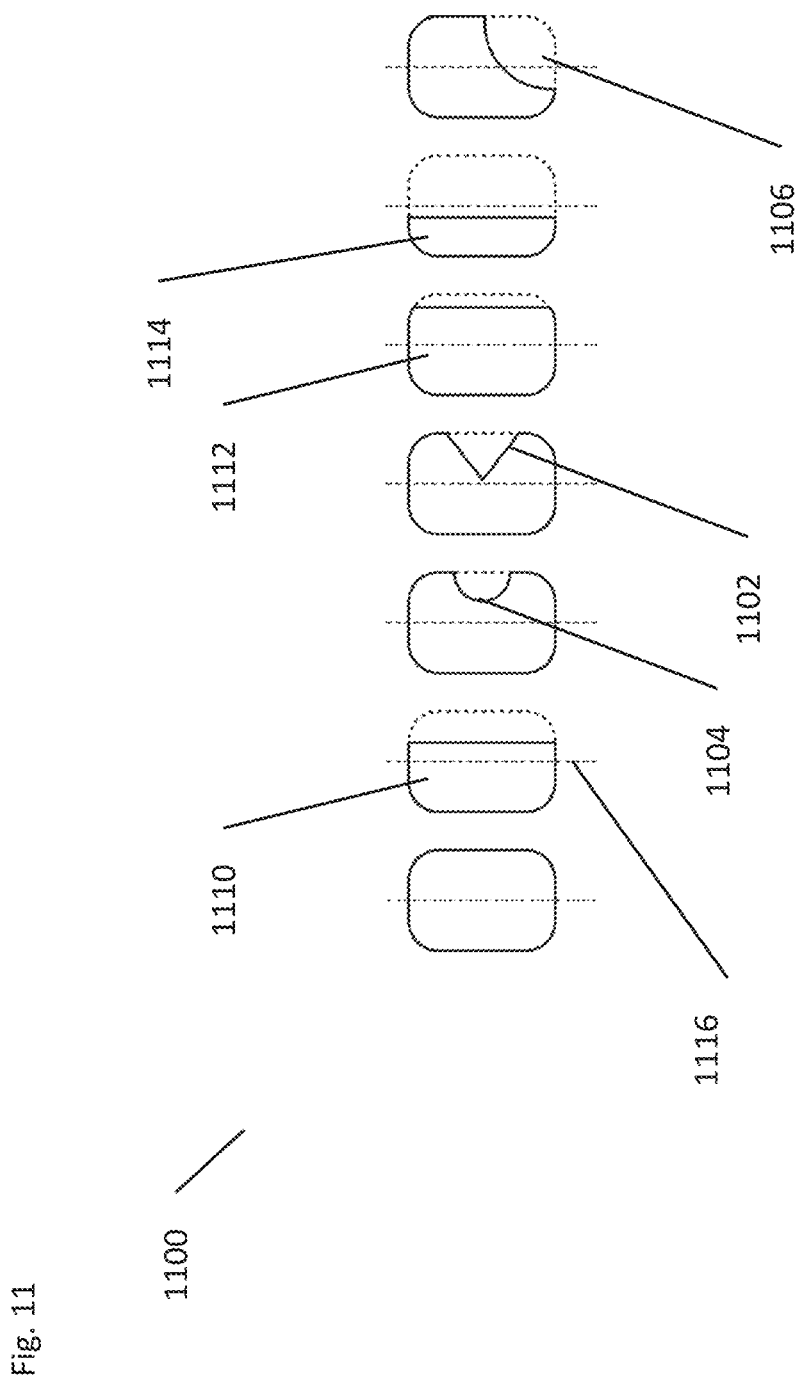
FIG. 11 illustrates various cross sections of compression relief mechanism in accordance with embodiments of the invention.

As illustrated throughout the figures, the relief can be configured in a number of different ways in a number of various embodiments. As such, FIG. 11 illustrates cross sectional views of various reliefs 1100 as applied to the rim of a menstrual device. Some relieves may be in the form of a notch where the notch can have a "V" shaped cross section 1102, a semicircle cross section 1104, or a quarter circle cross section 1106. Other embodiments may simply use a thinning of the rim (1110, 1112, and 1114) where the overall thickness of the rim in the leading lobe is thinner than that of the trailing lobe. Some embodiments may be thinned beyond the midline 1116 while others may be thinned to stop before the midline 1116. Although certain embodiments relief features are illustrated, it should be understood that any combination of reliefs may be used in conjunction with others and may be used separately or in combination with multiple durometer materials.

Figure 12:
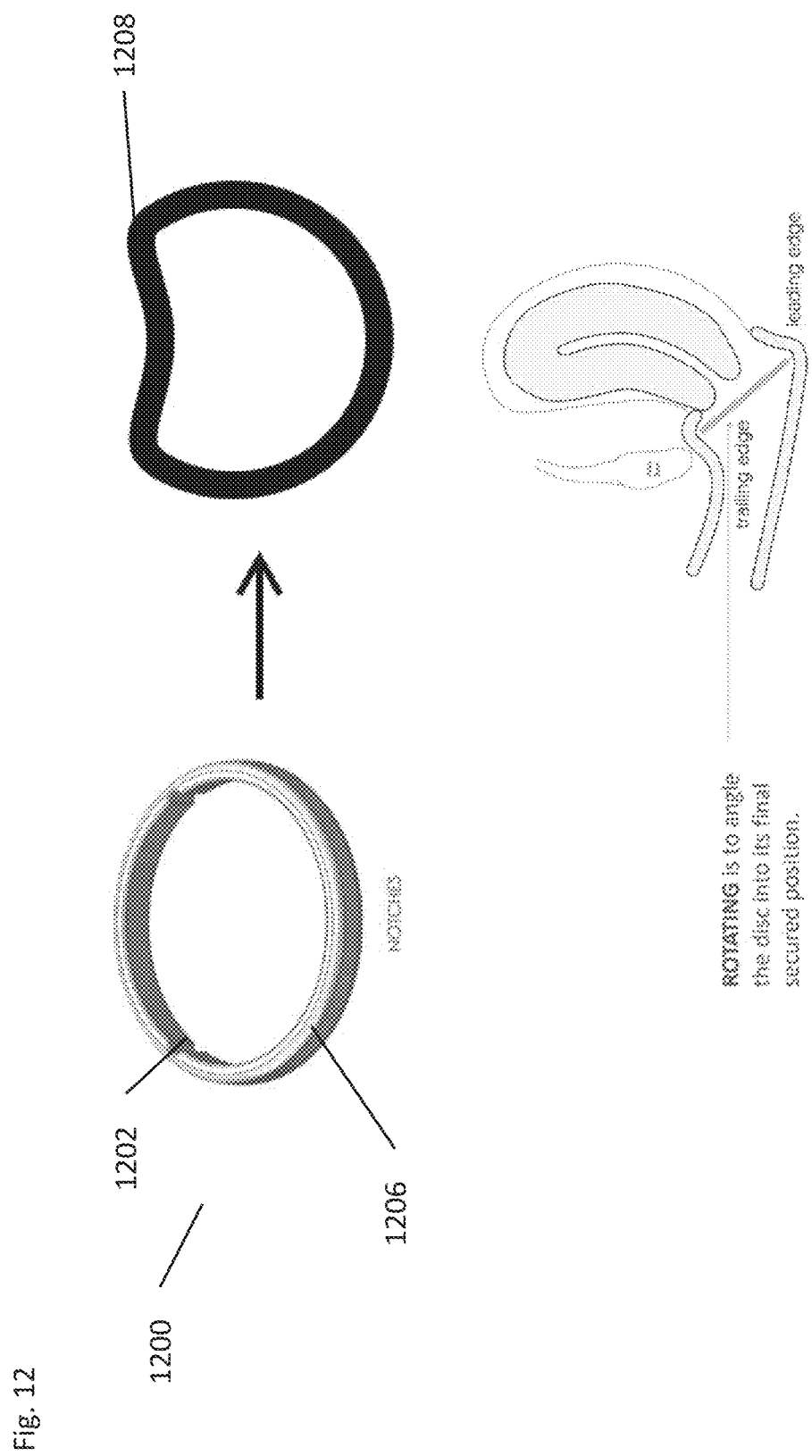
FIG. 12 illustrates the rim of a menstrual device in accordance with embodiments of the invention.

Turning now to FIG. 12, a menstrual device with more than one relief feature is illustrated. Relief features can serve a number of different functions, as described above. For example, many embodiments may have two or more relief features 1202 that are disposed circumferentially around the rim 1206. More than one relief feature 1202 can allow for multiple lobes 1208 to be formed when the device 1200 is folded. This can be beneficial for a variety of uses such as interacting with an applicator tool. Additionally, multiple lobes and/or relief features can assist a user in placing the device in the proper location.

Although the figures illustrate the placement of the relief mechanism or decompression feature at a particular position on the rim, it should be understood that the feature may be located anywhere on the rim. Additionally, the location of the relief feature may be referred to in radial degrees as it is located on a generally circular rim. For example, some embodiments may position the relief feature between 0.1 and 90 degree sweep. Other embodiments may place the relief feature between 0.1 and 45 degree sweep. Moreover, it should be understood that numerous embodiments can have a variety of transitions between the main body of the rim and the relief feature. For example, some relief features may have a smooth or gradual transition, such as, for example, in embodiments where the relief feature is a thinned portion of the rim. Other embodiments may have smooth or rounded edges indicating the location of the relief feature. Some embodiments of the relief feature, like the "V" shaped notch may have sharp transition edges between the body of the rim and the feature. Likewise, it should be understood that transitions can be smooth or gradual and that any transitions can be used individually or in combination with other transitions in accordance with various embodiments.

DOCTRINE OF EQUIVALENTS

As can be inferred from the above discussion, the above-mentioned concepts can be implemented in a variety of arrangements in accordance with embodiments of the invention. Specifically, menstrual devices with multiple durometer type materials that improve the form, fit, and function of the devices are illustrated. Achieving such functionality, according to embodiments, involves the implementation of special arrangements/designs between subsystems described above, and their equivalents.

Accordingly, although the present invention has been described in certain specific aspects, many additional modifications and variations would be apparent to those skilled in the art. It is therefore to be understood that the present invention may be practiced otherwise than specifically described. Thus, embodiments of the present invention should be considered in all respects as illustrative and not restrictive.

What is claimed is:

1. A menstrual device comprising:
   a body portion having an exterior surface and an interior surface and being made of a first material having a first durometer and defining a generally circular shape, wherein the interior surface defines a reservoir and wherein the exterior surface defines a first diameter;
   a resiliently foldable rim connected to the body portion and including an internal rim portion being made of a second material having a second durometer, the internal rim portion being surrounded by a remaining portion of the rim made of the first material, wherein the second durometer is higher than the first durometer.

2. The menstrual device of claim 1, wherein the body portion comprises an internal stiffener element disposed between the exterior surface and the interior surface and wherein the internal stiffener element is made of the second material.

3. The menstrual device of claim 1, further comprising a stem element connected to a bottom portion of the body, wherein the stem element has an elongated body that extends from the body portion downward beneath the body portion.

4. The menstrual device of claim 3, wherein the stem is made of a material having a durometer softer than the second durometer material.

5. The menstrual device of claim 1, wherein the rim has a cross sectional shape selected from a group consisting of triangular, "U" shaped, and curved upper and lower edges.

6. A menstrual device comprising
   a body portion having an exterior surface and an interior surface defining a generally circular shape, wherein the interior surface defines a reservoir and wherein the exterior surface defines a first diameter;
   a resiliently foldable rim connected to the body portion having an outer diameter and an inner diameter wherein the outer diameter is larger than the first diameter, wherein the rim has a predefined height and a rim thickness; and
   a notch disposed within the resiliently foldable rim, wherein the notch it extends from the inner diameter to a distance that is less than the rim thickness.

7. The menstrual device of claim 6, wherein the notch has a cross section selected from a group consisting of "V" shaped, semicircle, and quarter circle.

* * * * *